(12) United States Patent
Olson et al.

(10) Patent No.: US 9,658,146 B2
(45) Date of Patent: May 23, 2017

(54) ANALYSIS OF RECHARGEABLE BATTERIES

(71) Applicant: The Boeing Company, Chicago, IL (US)

(72) Inventors: Nels A. Olson, Seattle, WA (US); David C. Shangraw, Tukwila, WA (US); Douglas D. Maben, Snohomish, WA (US); Frederick B. McGalliard, Kent, WA (US); James D. Kinder, Bellevue, WA (US); John D. Jaquish, Auburn, WA (US); Jean-Philippe Belieres, Redmond, WA (US); Nikolay I. Shtanukhin, Woodinville, WA (US); Noel L. Spurlock, Federal Way, WA (US); Richard P. Lorenz, Woodinville, WA (US); Steven L. Baughcum, Redmond, WA (US)

(73) Assignee: The Boeing Company, Chicago, IL (US)

(*) Notice: Subject to any disclaimer, the term of this patent is extended or adjusted under 35 U.S.C. 154(b) by 506 days.

(21) Appl. No.: 14/188,592

(22) Filed: Feb. 24, 2014

(65) Prior Publication Data
US 2014/0241394 A1    Aug. 28, 2014

Related U.S. Application Data

(60) Provisional application No. 61/769,139, filed on Feb. 25, 2013, provisional application No. 61/769,158, filed on Feb. 25, 2013.

(51) Int. Cl.
*G01N 3/60* (2006.01)
*H01J 49/00* (2006.01)
(Continued)

(52) U.S. Cl.
CPC ............... *G01N 3/60* (2013.01); *G01N 21/17* (2013.01); *G01N 25/50* (2013.01); *G01N 30/88* (2013.01);
(Continued)

(58) Field of Classification Search
CPC .......... G01N 3/60; G01N 25/50; G01N 30/88; G01N 21/17; G01N 25/4846; H01M 10/4285; H01M 10/42; H01J 49/0036
See application file for complete search history.

(56) References Cited

U.S. PATENT DOCUMENTS 4,439,048 A * 3/1984 Townsend ............... G01K 17/00
374/34
8,313,850 B1 * 11/2012 LePort .................. H01M 10/42
429/50

(Continued)

OTHER PUBLICATIONS

Perrine Ribiere et al., "Investigation on the fire-induced hazards of Li-ion battery cells by fire calorimetry", Energy Environ.Sci, vol. 5, No. 1, pp. 5271-5280 (Sep. 22, 2011).
(Continued)

*Primary Examiner* — Michael A Lyons
*Assistant Examiner* — Philip Cotey
(74) *Attorney, Agent, or Firm* — Miller, Matthias & Hull LLP

(57) ABSTRACT

A rechargeable battery is externally heated to induce thermal runaway, and material expelled from the battery is analyzed.

28 Claims, 5 Drawing Sheets

(51) Int. Cl.
- *G01N 21/17* (2006.01)
- *G01N 25/50* (2006.01)
- *G01N 30/88* (2006.01)
- *H01M 10/42* (2006.01)
- *H01M 10/48* (2006.01)
- *G01N 25/48* (2006.01)

(52) U.S. Cl.
CPC ......... *H01J 49/0036* (2013.01); *H01M 10/42* (2013.01); *H01M 10/486* (2013.01); *G01N 25/4846* (2013.01)

(56) References Cited

U.S. PATENT DOCUMENTS

| | | | |
|---|---|---|---|
| 2001/0030987 A1* | 10/2001 | Plotnikov | G01N 25/4806 374/10 |
| 2006/0028173 A1* | 2/2006 | Sellers | H01M 2/1022 320/112 |
| 2006/0125483 A1* | 6/2006 | Bertness | G01R 31/3624 324/426 |
| 2014/0003460 A1* | 1/2014 | Keyser | G01K 17/00 374/31 |

OTHER PUBLICATIONS

Roth et al., "Advanced Technology Development Program for Lithium-Ion Batteries: Thermal Abuse Performance of 18650 Li-Ion Cells," Sandia Report SAND2004-0584, pp. 1-139, XP055122702. (Mar. 1, 2004).

Crafts et al., "Safety Testing of 18650-Style Li-Ion Cells," Sandia Report SAND2000-1454C, pp. 1-6, XP055123024 (Jun. 20, 2000).

Doughty et al., "FreedomCAR, Electrical Energy Storage System, Abuse Test Manual for Electric and Hybrid Electric Vehicle Applications," Sandia Report SAND2005-3123, pp. 1-47, XP055122726 (Aug. 1, 2006).

Abraham et al., "Diagnostic examination of thermally abused high•power lithium-ion cells", Journal of Power Sources, vol. 161, No. 1, pp. 648-657 (May 30, 2006).

Doughty et al., "A general discussion of Li Ion battery safety," The Electrochemical Society Interface, pp. 37-44 (2012).

* cited by examiner

ANALYSIS OF RECHARGEABLE BATTERIES

This application claims the benefit of provisional application 61/769,139 filed 25 Feb. 2013, and provisional application 61/769,158 filed 25 Feb. 2013, both of which are incorporated herein by reference.

BACKGROUND

Lithium-ion (Li-ion) batteries (LIBs) are desirable for mobile computing devices, certain automobiles, and certain aircraft. They have lower weight and higher energy density than rechargeable batteries such as nickel metal hydride and nickel cadmium batteries. They have no memory degradation.

However, certain lithium-ion batteries have longstanding issues with thermal runaway. As used herein, thermal runaway means a situation where an increase in temperature causes a further increase in temperature that may lead to decreased efficiency. For example, heat generated from an exothermic chemical reaction may increase the rate of the chemical reaction. Designers of complex systems may address such inefficiencies in various ways.

SUMMARY

According to an embodiment herein, a method of analyzing a rechargeable battery comprises externally heating the battery to induce thermal runaway; and analyzing material expelled from the battery.

According to another embodiment herein, a method comprises placing a rechargeable battery in a test vessel, externally heating the battery to cause the battery to rupture, capturing material expelled by the battery following the rupture, and analyzing the captured materials. The analysis includes toxicology analysis on the captured materials.

According to another embodiment herein, an apparatus comprises a pressure vessel, a rechargeable battery within the pressure vessel, means for externally heating the battery within the pressure vessel to induce thermal runaway, and means for collecting material expelled by the battery during the external heating.

These features and functions may be achieved independently in various embodiments or may be combined in other embodiments. Further details of the embodiments can be seen with reference to the following description and drawings.

DETAILED DESCRIPTION

Figure 1:
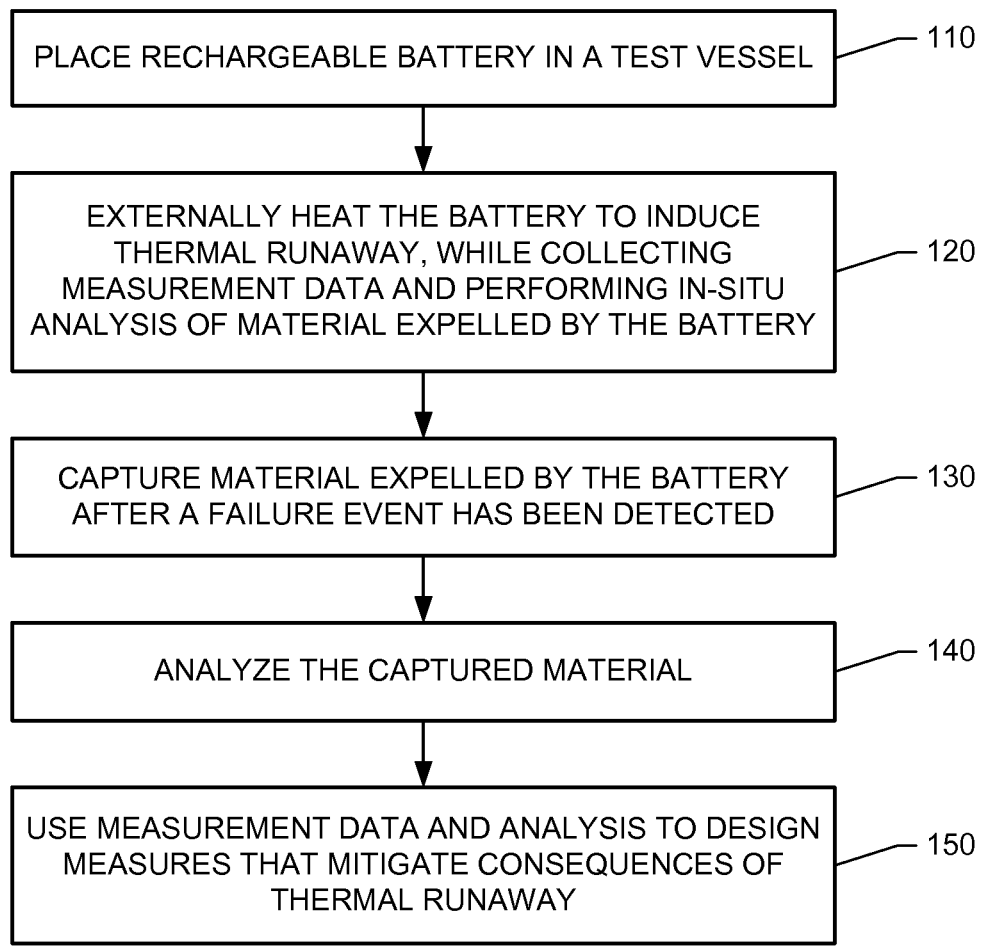
FIG. 1 is an illustration of a method of analyzing a rechargeable battery.

Reference is made to FIG. 1, which illustrates a method of analyzing a rechargeable battery. The rechargeable battery may include one or more battery cells. Each battery cell may include positive and negative electrodes, an electrolyte, and an outer case for the electrodes and the electrolyte. The rechargeable battery is not limited to any particular chemistry. Examples include, but are not limited to lithium-ion, metal-cadmium, nickel-metal hydride, and lead-acid. Depending on the battery chemistry, the rechargeable battery may be susceptible to thermal runaway.

At block 110, the rechargeable battery is placed in a test vessel. If the battery is enclosed in a metal enclosure during normal usage, the enclosure may also be placed in the test vessel, with the battery inside. If the battery is used with other another structure during normal battery operation, that other structure may be placed in the test vessel and tested along with the battery.

Prior to external heating, the battery may be charged, and its voltage measured. Battery charge state defines the some of the internal processes important to battery operation.

At block 120, the battery is externally heated. In some embodiments, the heating may be performed until a battery failure event (e.g., rupture) is detected. In other embodiments, the heating may be performed to observe slower processes that eventually cause thermal runaway. During heating, measurement data may be collected during the testing and recorded. Examples of measurement data include temperature, pressure, and relative humidity data.

The external heating may induce thermal runaway. In a lithium-ion battery cell, for instance, a first type of thermal runaway is caused by an overall slower process at relatively low temperatures in the vicinity of 80° C. This first type of runaway is caused by chemical degradation processes at the solid electrolyte interface (SEI). A battery cell of the lithium ion type, held at 80° C. can and often does experience a slow degradation in the SEI which builds in magnitude until a battery cell starts to increase in temperature at a rapid rate. The thermal runaway can cause a battery failure such as a rupture. Another type of failure is metal corrosion.

As the battery cell crosses the temperature range of 130-150° C., a type of thermal runaway becomes more prevalent. A polymer-based separator between the charge collectors (coated foil) begins to bread down. The battery short circuits at locations where the polymer separator has failed, heat increases, and eventually the battery exceeds its pressure rating and ruptures.

The external heating may be performed in several ways. As a first example, the entire test vessel may be heated. As a second example, the interior of the test vessel is heated. As a third example, only the battery is heated. As a fourth example, the battery is heated with heating structures placed proximal to the battery. As a fifth example, the battery is heated using a combination of two or more of the four examples above.

The external heating may be controlled to follow a desired heating profile. Different failure mechanisms may be accessed by different rates of heating. Slow heating allows two mechanisms of failure to be engaged: 1) SEI failure; and 2) entire cell simultaneous failure (rather than progressive failure). Slow heating means that the battery is held at a temperature that is high but below the critical temperature where the self-propagation curve meets with the exponential heating curve. Generally the slow heating is done at or near 80° C. and can take a few days.

Rapid heating is more relevant to cell-to-cell propagation. If one battery cell fails from thermal runaway, neighboring cells are rapidly heated by the failing battery cell. The rapidity of heating may be defined by contact between the battery cells, how well they are insulated from one another, and the dynamics of the failing cell.

For example, the ambient temperature starts at around 60° C. (i.e., hot). The battery cell is then allowed to go through the various processes both slow and rapid where to a point where self-heating starts to occur.

Figure 5:
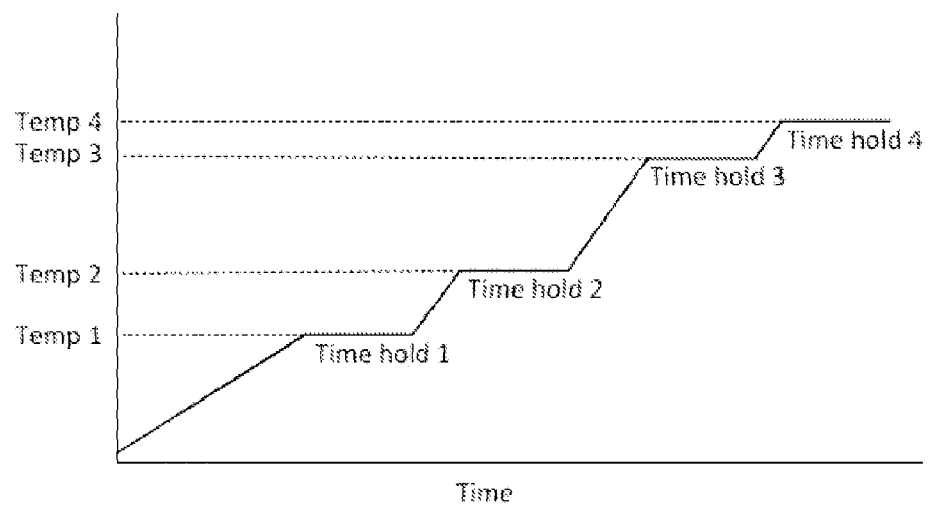
FIG. 5 is an illustration of a heating profile during battery testing.

FIG. 5 provides an example of a heating profile. This profile illustrates different rates and dwell times of heating a rechargeable battery during testing, Temperature is increased and held, increased and held, increased and held, and increased and held to a point where self-heating starts to occur.

Rupture may refer to any of three types of release of pressure. The first type is a release of pressure that occurs slowly via leaking around electrical connections (e.g., the terminals). The second type is a rupture of a protection mechanism (e.g., a rupture plate covering a vent hole in the case) that allows a rapid decompression of the battery cell case. This second type of rupture can result in a loss of liquid electrolyte solvent and solid materials. The third type occurs after the rupture of a protection mechanism. The protection mechanism becomes clogged by debris and causes the battery cell case to part at the seams.

A battery failure event such as a rupture may be detected by monitoring temperature and/or pressure of the battery, as there is a fast rise in temperature and pressure during rupture. A battery failure event such as a rupture may instead be determined by monitoring temperature of any material expelled by the battery cell. For instance, if the battery cell has a rupture plate covering a vent hole, temperature may be monitored at the rupture plate. Any material expelled through the vent hole will be hot.

At block 130, once a battery failure event has been detected, expelled material is captured. The expelled material may be captured in containers. Liquids, solids and gases may be stored in separator containers. Measures may be taken to remove particles from gases released from the battery. Particle removal may be performed to keep particles out of containers that store gases. Particle removal may also reveal the types of aerosols that are produced and the distances that they travel.

During block 120 and at block 140, the material expelled from the battery is analyzed. Gases generated by the battery may be analyzed during battery failure. Gases, solids and liquids collected after battery failure may be analyzed. Electrolyte liquids under stress may be analyzed prior to battery failure.

The following types of analysis may be performed. Toxicology analysis may be performed. The toxicology analysis involves comparing collected materials to likely products based on battery and pyrolysis chemistry. The toxicology analysis may also involve a comparison of the collected materials against toxicology data (that is, comparing the collected materials against lists of toxic chemicals).

Compatibility analysis may be performed. The compatibility analysis involves the compatibility of materials that are proximal to the battery. For instance, if the battery is enclosed in an enclosure, then the compatibility analysis may be performed between the expelled materials and enclosure materials, such as coatings, paints, sealants, electrical components, electronics, and insulation. Compatibility analysis may include post failure analysis of materials proximal to the battery via visual inspection, standard mechanical tests, and spectroscopic non-destructive tests.

Gas chromatography/mass spectrometry (GC/MS) head space analysis may be performed. Head space is analysis of the gas space above the sample in a container. Volatile sample components diffuse into the gas phase, forming the headspace gas. Head space analysis is therefore the analysis of the components present in that gas. This analysis involves identifying those elements in the gas (above a complex sample) that are volatile at a particular temperature.

Micro-probe analysis of solid residue of the expelled material may be performed. An electron microprobe (EMP), also known as an electron probe microanalyzer (EPMA) or electron micro probe analyzer (EMPA), may be used to non-destructively determine the chemical composition, or chemical makeup, of small volumes of captured solids. The volume is bombarded with an electron beam, emitting x-rays at wavelengths characteristic to the elements being analyzed. The micro-probe analysis can reveal the quantitative relationship between the elements (types of atoms) released from the battery upon failure. This analysis reveals the origin of the materials because specific elements can be mapped back to the base material from which they came.

Infrared gas cell analysis for light components may be performed. The infrared analysis can reveal real-real time compositional information during battery failure. An infrared gas analyzer measures trace gases by determining the absorption of an emitted infrared light source through a certain gas sample. Gas vibrational modes are excited under specific wavelengths found in the infrared range. Different molecules in the gas absorb different frequencies of light. Gas mixtures with a lot of a certain component gas will absorb more of a certain frequency, whereby a high concentration of the corresponding molecule or chemical functional group will be detected. This analysis reveals where molecules came from and what happened to them in the process of battery failure. The infrared gas analysis may be performed as the battery is being heated, and/or it may be performed on a static sample post failure.

Ion-exchange chromatography (or ion chromatography) may be performed. Ion-exchange chromatography allows the separation of ions and polar molecules based on their affinity to the ion exchange resin in separation column. The ion-exchange chromatography may be used to look for ions that are important to battery operation and that may be released during battery failure. For determining toxicity from hydrogen fluoride (HF) released from battery cells, ion-exchange chromatography may be used to measure the fluoride ions produced in a quantitative way.

Inductively Coupled Plasma (ICP) spectroscopy may be performed. ICP is a type of plasma source in which energy is supplied by electric currents produced by electromagnetic induction, via time-varying magnetic fields. The plasma excites atoms in a vaporized sample introduced to the plasma flame that can then be measured in a quantitative way by their emitted light. ICP may be used to measure metals in the solids and liquids produced during battery failure. Measurements of the metals provide information about their origin and how much of them are present.

Flammability analysis may be performed. The flammability analysis may be performed on collected materials. The flammability analysis may be performed in-situ (as the battery is being heated) at varying temperatures and concentrations of air in the test vessel. The flammability analysis may be performed with or without the use of artificial ignition source. The artificial ignition source mimics the battery as the source of ignition, but where deflagration is being tested. If an artificial ignition source is not used and no deflagration occurs, the battery cell itself is not the source of the ignition energy.

During heating of the battery at block 120 and during material capture at block 130, environmental conditions in the test vessel may be varied. As a first example, a turbulent flow of gas may be created to either enhance the collection of particles or remove particles from the gas mixture prior to analysis. For instance, circuitous path scrubbers may be used to remove particles from gases released from the battery.

During heating of the battery at block 120 and after cell rupture, normal operating pressures for the battery may be simulated. Consider a first example of an aircraft having a battery that is contained within a metal enclosure. During normal usage, the outside of the enclosure is subjected to pressure cycles, which change due to changes in atmospheric pressure. The enclosure may be vented via orifices so that pressures inside and outside the enclosure are equalized. This pressure equalization allows the battery to experience the pressurization of the aircraft cabin instead of the larger altitude based atmospheric pressure. Analysis of any material expelled by the battery would indicate whether the pressure equalization had any effect on battery failure.

Consider a second example of a battery that is contained within a metal enclosure during normal usage, and further consider that the enclosure is vented when a pressure differential between pressures inside and outside the enclosure exceeds a limit. Heat is applied externally until the limit is exceeded. Analysis of any material expelled by the battery could indicate whether the venting had any effect on battery failure.

The venting during testing provides an additional benefit. It enables vent dynamics and temperature gradients out the vent to be analyzed.

Now consider a third example, which involves charging of a battery according to a profile. Tests can be conducted for different charging profiles.

At block 150, the measurement data and analysis is used to design measures that mitigate consequences of thermal runaway in the rechargeable battery. The method also enables the designs to be implemented and evaluated.

The applicant performed the method on rechargeable batteries for aircraft. One such battery was a lithium cobalt oxide ($LiCoO_2$) battery. Approaches for mitigating consequences of thermal runaway and determining battery failure parameters were learned from exothermic reaction monitoring during battery heating. The measurement data and analysis had an influence on designs for an enclosure for a rechargeable battery, a vent system for a rechargeable battery, a chassis for a rechargeable battery, and thermal separators for battery cells of a rechargeable battery. The measurement data and analysis also had an influence on design of a profile for charging a rechargeable battery.

Figure 2:
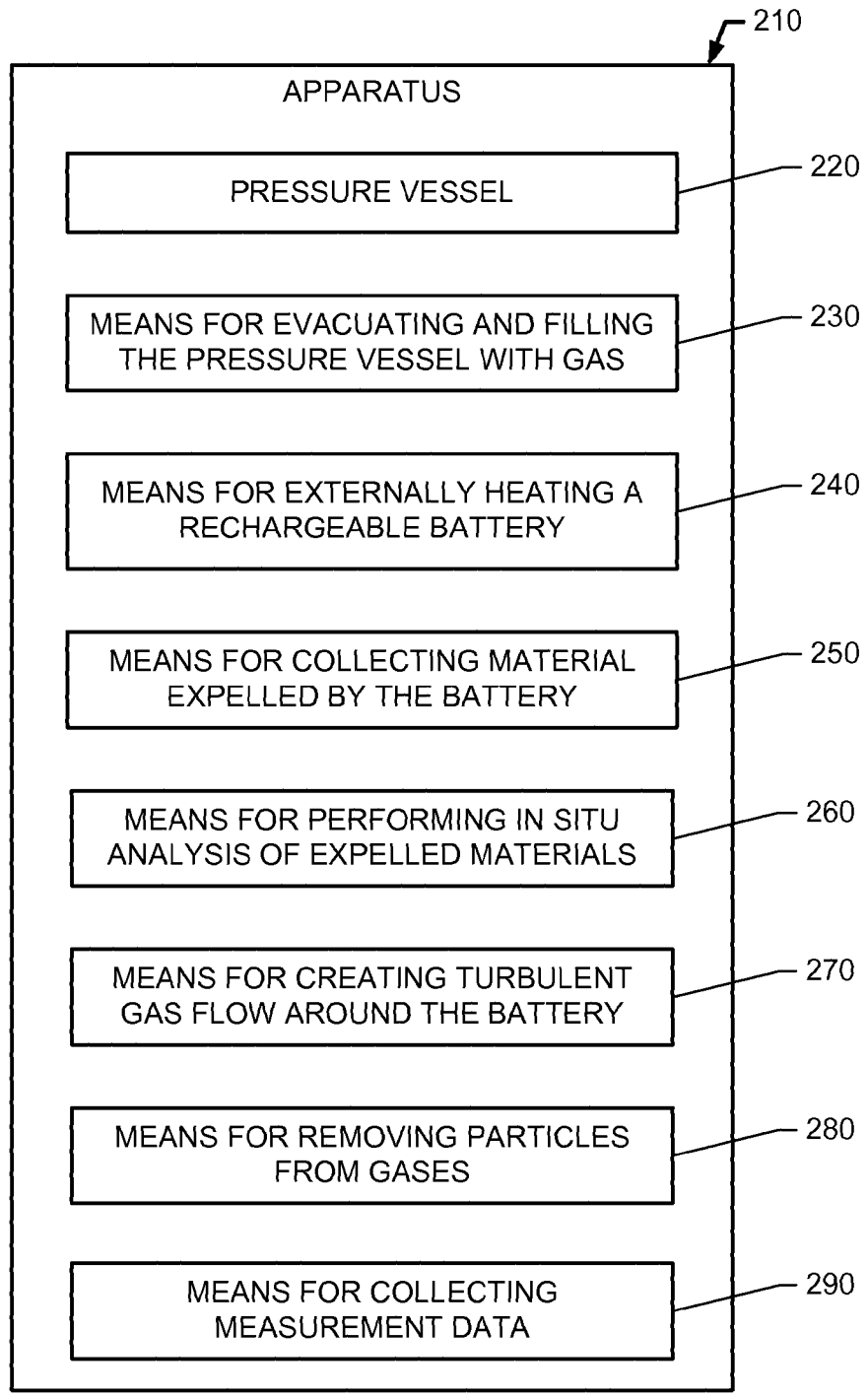
FIG. 2 is an illustration of various components of an apparatus for analyzing a rechargeable battery.

Reference is now made to FIG. 2 which illustrates various components of an apparatus 210 that collects measurement data and supports analysis of a rechargeable battery. The apparatus includes a pressure vessel 220. During testing, the battery is located inside the pressure vessel 220.

The apparatus 210 includes means 230 for evacuating the pressure vessel 220 and also filling the pressure vessel 220 with different types of gases. The pressure vessel 220 may be filled with different types of gases to support different types of tests that determine different aspects of the chemical dynamics at battery failure. Consider the following three examples. In the first example, the pressure vessel 220 is evacuated to ensure that there is no available oxygen and as little other gases present as possible.

In the second example, the pressure vessel 220 is pumped and purged with argon or another noble gas. The noble gas avoids unintended reactivitiy with materials expelled by the battery. This example may be used to study the effect or gas that surrounds the battery.

In the third example, the pressure vessel 220 is filled with air or air mixtures with other gases to determine the effect of oxygen, or other gases on the chemical mechanisms of battery failure.

The apparatus 210 includes means 240 for externally heating the battery within the pressure vessel 220. Examples of the means 240 are provided below.

The apparatus 210 includes means 250 for collecting material expelled by the battery. The material may be collected under deflagration events on the order of milliseconds. The materials may be captured and evacuated into storage containers. Different storage containers may be provided for the separate collection of solids, liquids, gases, and aerosols of various particle sizes.

The apparatus 210 may further include means 260 for performing in situ analysis of the expelled materials to determine physical and chemical properties. The means 260 may include, for example, an electron probe microanalyzer for micro-probe analysis of solid residue, and an infrared gas analyzer.

The means 260 for in situ analysis may further include an artificial ignition source for flammability analysis of materials expelled by the battery. The artificial ignition source may include an igniter and a controller for operating the igniter in a continuous mode and an intermittent mode. The intermittent mode allows materials to be released from the battery prior to ignition. This is done to allow different concentrations of fuel molecules to escape from the battery cell prior to those gases coming in contact with the ignition source.

The apparatus 210 may further include a means 270 for creating turbulent gas flow around the battery. The means 270 may include a gas diffuser.

The apparatus 210 may include means 280 for removing particles from gases released from the battery. For example, the means 280 may include circuitous path scrubbers, which can remove sub-micrometer particles efficiently, and can function well in hot or corrosive environments.

The apparatus 210 may further include means 290 for collecting measurement data. The means 290 may include a plurality of dedicated data measurement devices for temperature, pressure, humidity, etc. If the battery cell is equipped with a battery monitoring unit (BMU), the BMU may perform these measurements instead of, or in addition to, the dedicated data measurement devices.

Figure 3:
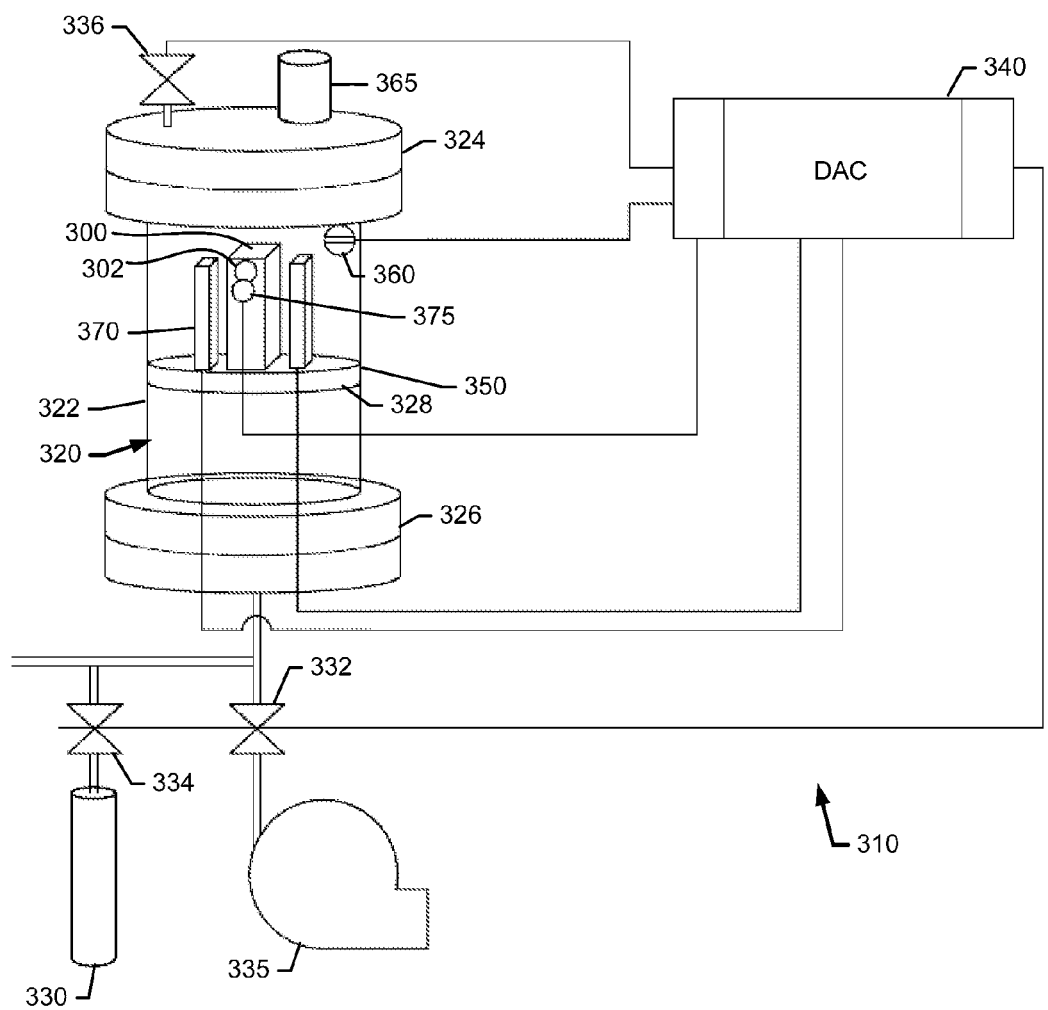
FIG. 3 is an illustration of an apparatus for analyzing a rechargeable battery.

Reference is now made to FIG. 3, which illustrates an apparatus 310 for analyzing a rechargeable battery 300. The apparatus 310 includes pressure vessel 320 formed by sidewalls 322, a top closure 324, and a base closure 326. The sidewalls 322 and closures 324 and 326 may be made of a corrosion resistant material (e.g., 304 stainless steel, 316 stainless steel) and designed to withstand test requirements (e.g., a pressure rating of approximately 1050 psig). The pressure vessel 320 further includes a shelf 328 secured to the sidewalls 322. The shelf 328 holds the battery 300 securely during a testing cycle.

The apparatus 310 includes a plurality of cylinders 330 for collecting material expelled by the battery. Samples may be admitted to the cylinders 330 via solenoid valves 334.

Another solenoid valve 332 enables a vacuum to be applied to the pressure vessel 320. The vacuum may be applied via a port in the base closure 326. The vacuum may be created by a vacuum source 335 such as a vacuum pump. The solenoid valve 332 may be vacuum-rated, and it may be used to isolate the pressure vessel 320 from the vacuum source 335.

Testing under vacuum conditions may be performed to eliminate gases from the atmosphere and thus reveal those gases coming from the battery. For instance, the testing under vacuum conditions can reveal whether the battery is producing its own oxygen.

Another solenoid valve 336 enables inert gas to be supplied to the pressure vessel 320. The inert gas may be supplied via a port in the base closure 326. An inert gas regulator and cylinder (not shown) may be used to supply the inert gas. Filling the pressure vessel with inert gas enable battery failure to be studied without oxygen but under pressure.

The solenoid valves 332-336 may be controlled by a personal computer-based data acquisition and control (DAC) system 340. The DAC system 340 may be programmed to sequence the opening and closing of the solenoid valves 332-336 after a battery failure event to collect samples at specified time intervals. The DAC system 340 may also be programmed to collect and store measurement data (e.g., pressure, temperature).

The apparatus 310 further includes a heater 350 inside the pressure vessel 320 for externally heating the battery 300. The heater 350 may include one or more heating pads.

The apparatus 310 further includes an igniter 360 inside the pressure vessel 320. The igniter 360 supports flammability testing of materials expelled by the battery 300.

The pressure vessel 320 may include a vent port 365 fitted with a diaphragm (not shown) that is designed to rupture when pressure inside the pressure vessel 320 reaches a limit. A vent tube (not shown) may be attached to the vent port 365.

The vent tube may be identical to the tube actually used during normal usage of the battery. The vent tube may, for example, match in length, material, radius of turns, length of straight components, number of turns, joints between sections, etc.

The apparatus 310 may further include sensors for measuring temperature of the vent tube in multiple locations, and sensors for measuring mass flow through vent tube. The sensors can identify points on the vent tube that get too hot.

The apparatus 310 may also include a vent temperature sensor 375 located over a rupture plate 302 of the battery 300. When the rupture plate 302 is ruptured, material expelled from battery 300 will cause a sharp rise in temperature sensed by the vent temperature sensor 375. The DAC system 340 may look for a spike in the sensed temperature, or it may compare the sensed temperature to a threshold. When the spike occurs or the threshold is exceeded, the DAC system 340 may perform various actions including opening and closing valves to ensure the best quality samples are collected and ancillary equipment is protected.

The apparatus 310 may include surfaces (not shown) for collection of solids. In addition, solids and liquids may be collected via a drain (not shown) at an underside of the base closure 326.

The apparatus 310 further includes instrumentation for collecting measurement data during testing. To measure pressure, a pressure port in one of the closures 324 or 326 may be connected to a pressure transducer (not shown) or a pressure probe such as a pitot static probe (not shown). To measure temperature, a temperature monitor 370 including a plurality of thermocouples may be located within the pressure vessel 320. To measure voltage, a pair of leads connected to the battery's terminals may be monitored. To measure oxygen, an oxygen sensor (not shown) may be installed in the top closure 324.

Figure 4:
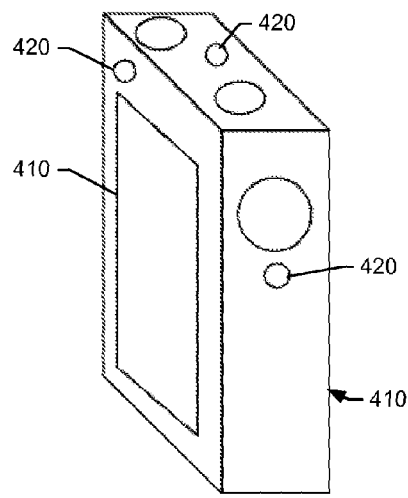
FIG. 4 is an illustration of a rechargeable battery equipped for external heating and temperature sensing.

Additional reference is made to FIG. 4, which provides an example of how a rechargeable battery cell 400 may be equipped for external heating. A heating pad 410 may be secured to one or both sides of the battery cell 400. Each heating pad 410 may include a resistive electrical pad that is adhered to the battery cell 400 via high temperature tape so as not to unduly increase the battery's thermal mass.

FIG. 4 also provides an example of locations for a plurality of temperature measurement devices such as thermocouples 420 for sensing temperature of the battery cell 400 during testing. The thermocouples 420 are placed on a surface of the battery cell 400. One of the thermocouples 420 may be placed near the battery cell's rupture plate 402.

Figure 6:
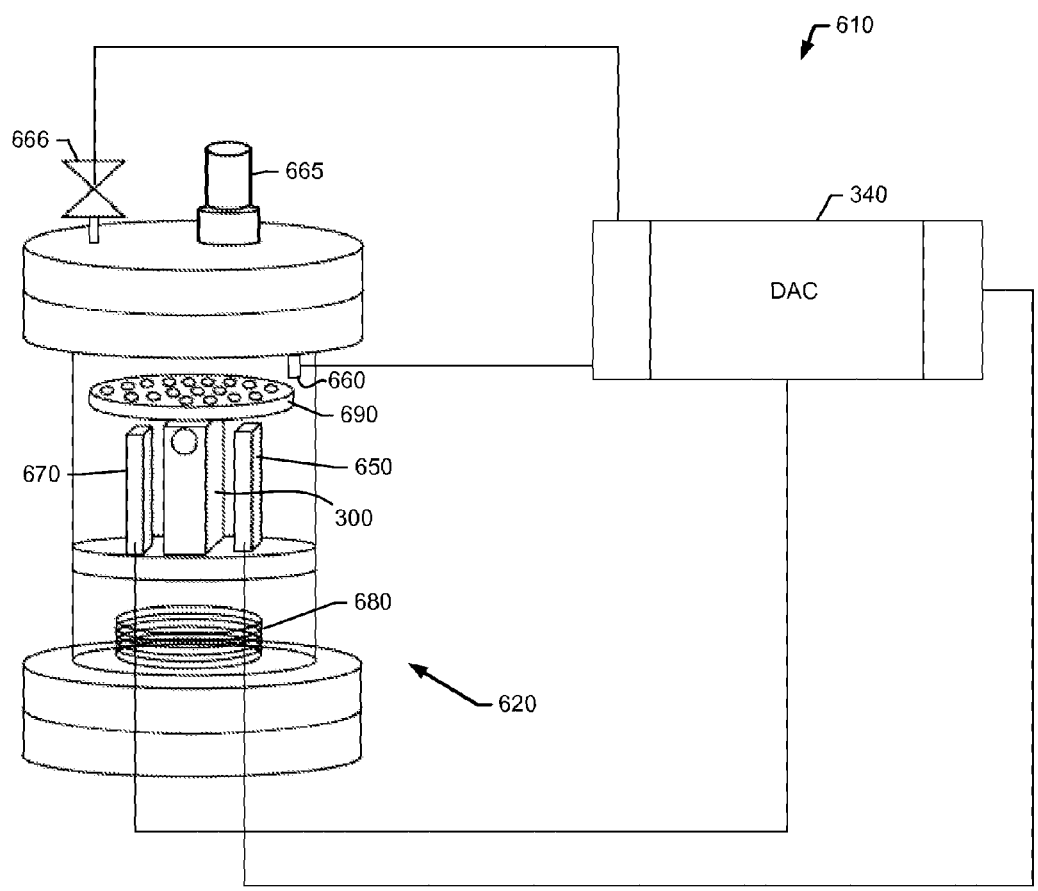
FIG. 6 is an illustration of an apparatus for analyzing a rechargeable battery.

FIG. 6 is an illustration of another apparatus 610 for analyzing a rechargeable battery 300. The apparatus 610 includes a pressure vessel 620 having a similar construction as the pressure vessel 320 of the apparatus 310 of FIG. 3. The apparatus 610 also includes valves (not shown) for controlling the collection of samples, valves (not shown) for purging and introducing gases into the pressure vessel 620, a DAC system 640, a battery heater 650, an igniter, 660, a vent 665, and a battery temperature monitor 670. The apparatus 610 further includes a valve 666 for opening and closing the vent 665.

The apparatus 610 of FIG. 6 not only heats the battery 300 externally, but also varies the internal temperature of the pressure vessel 620. The internal temperature may be varied by a steam coil 680 within the pressure vessel 620. The steam coil 680 may include a coil of copper tubing. An external steam source (not shown) may supply steam to the steam coil 680 via a valve (not shown), which is controlled by the DAC system 640. Condensate in the pressure vessel 620 may be drained via a steam trap.

The apparatus 610 may further include a gas diffuser 690. The gas diffuser may include a perforated disk mounted above the battery 300. The disk does not allow gases to go directly out the vent 665. The perforations in the disk force the gases to take a more circuitous path.

The invention claimed is:

1. A method of analyzing a rechargeable battery design, the method comprising:
   a vacuum test including:
      placing a first rechargeable battery in a test vessel;
      evacuating the test vessel;
      externally heating the first battery to induce thermal runaway;
      monitoring a temperature and a pressure inside the test vessel to detect a rupture of the first battery; and
      when the rupture of the first battery is determined, analyzing material expelled from the first battery following the rupture to obtain test data under vacuum conditions;
   a noble gas test including:
      placing a second rechargeable battery in the test vessel;
      purging the test vessel with a noble gas;
      externally heating the second battery to induce thermal runaway;
      monitoring a temperature and a pressure inside the test vessel to detect a rupture of the second battery; and
      when a rupture of the second battery is determined, analyzing material expelled from the second battery following the rupture to obtain test data under noble gas conditions; and an oxygen test including:
  placing a third rechargeable battery in a test vessel;
  filling the test vessel with air;
  externally heating the third battery to induce thermal runaway;
  monitoring a temperature and a pressure inside the test vessel to detect a rupture of the first battery; and
  when a rupture of the first battery is determined, analyzing material expelled from the third battery following the rupture to obtain test data under oxygen conditions.

2. The method of claim 1, wherein the battery is externally heated at varying rates.

3. The method of claim 1, further comprising performing exothermic reaction monitoring during battery heating.

4. The method of claim 1, wherein a structure used with the battery during normal battery operation is tested along with the battery; and wherein compatibility analysis between the structure and the expelled material is performed.

5. The method of claim 4, wherein the structure includes a metal enclosure for the battery.

6. The method of claim 1, wherein the analysis includes toxicology analysis on the expelled material.

7. The method of claim 1, wherein the analysis includes determining chemical composition of components of the expelled material.

8. The method of claim 1, wherein the analysis includes gas chromatography/mass spectrometry (GC/MS) head space analysis.

9. The method of claim 1, wherein the analysis includes micro-probe analysis of solid residue from the expelled material.

10. The method of claim 1, wherein the analysis includes infrared gas cell analysis for light components.

11. The method of claim 1, wherein the analysis includes ion-exchange chromatography.

12. The method of claim 1, wherein the analysis includes Inductively Coupled Plasma (ICP) Spectroscopy.

13. The method of claim 1, wherein the analysis includes flammability analysis.

14. The method of claim 13, wherein the flammability analysis is performed in an intermittent mode to allow materials to be released from the battery prior to ignition.

15. The method of claim 1, further comprising creating a turbulent flow of gas during the external heating.

16. The method of claim 1, further comprising removing particles from gases expelled by the battery.

17. The method of claim 1, wherein during the heating, the battery is contained within an enclosure, the enclosure is subjected to pressure cycles, and equalization between pressures inside and outside the enclosure is performed.

18. The method of claim 17, further comprising venting the enclosure.

19. The method of claim 1, further comprising using the analysis to design measures for mitigating consequences of thermal runaway in the rechargeable battery.

20. An apparatus for testing a rechargeable battery design, the apparatus comprising:
  a pressure vessel;
  means for selectively evacuating the pressure vessel;
  means for selectively purging the pressure vessel with a noble gas;
  means for selectively filling the pressure vessel with air;
  means for externally heating a battery within the pressure vessel to induce thermal runaway and cause the battery to rupture and expel material;
  means for collecting material expelled by the battery during the external heating and following the rupture when:
    the pressure vessel is evacuated by the means for selectively evacuating the pressure vessel to obtain test data under vacuum condition;
    the pressure vessel is purged with noble gas by the means for selectively purging the pressure vessel with the noble gas to obtain test data under noble gas conditions; and
    the pressure vessel is filled with air by the means for selectively filling the pressure vessel with air to obtain test data under oxygen conditions.

21. The apparatus of claim 20, further comprising means for in situ analysis of the expelled materials to determine physical and chemical properties.

22. The apparatus of claim 20, further comprising means for creating turbulent gas flow around the battery.

23. The apparatus of claim 20, further comprising means for removing particles from gases expelled by the battery.

24. The apparatus of claim 20, further comprising means for performing flammability analysis on materials expelled by the battery.

25. The apparatus of claim 24, wherein the means for performing flammability analysis includes an igniter operable in a continuous mode and an intermittent mode.

26. The apparatus of claim 20, further comprising an enclosure for the battery.

27. The apparatus of claim 26, further comprising a vent attached to the enclosure, the vent configured for normal usage with the battery.

28. The apparatus of claim 20, further comprising a plurality of temperature measurement devices on a surface of the battery.

* * * * *